United States Patent
Jin et al.

(10) Patent No.: US 11,795,076 B2
(45) Date of Patent: Oct. 24, 2023

(54) SYNTHESIS METHOD OF INDOLE DERIVATIVE CAPABLE OF EFFICIENTLY DEGRADING PERFLUORINATED COMPOUND (PFC)

(71) Applicant: Nanjing University, Nanjing (CN)

(72) Inventors: Xin Jin, Nanjing (CN); Cheng Gu, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 17/920,816

(22) PCT Filed: Apr. 2, 2021

(86) PCT No.: PCT/CN2021/085306
§ 371 (c)(1),
(2) Date: Oct. 24, 2022

(87) PCT Pub. No.: WO2021/218570
PCT Pub. Date: Nov. 4, 2021

(65) Prior Publication Data
US 2023/0167055 A1 Jun. 1, 2023

(30) Foreign Application Priority Data
Apr. 29, 2020 (CN) .......................... 202010353919.4

(51) Int. Cl.
C02F 1/58 (2023.01)
C02F 1/28 (2023.01)
(Continued)

(52) U.S. Cl.
CPC .............. *C02F 1/583* (2013.01); *C02F 1/285* (2013.01); *C02F 1/68* (2013.01); *C02F 2101/36* (2013.01);
(Continued)

(58) Field of Classification Search
None
See application file for complete search history.

(56) References Cited

FOREIGN PATENT DOCUMENTS

| CN | 101884831 A | 11/2010 |
|---|---|---|
| CN | 104549179 A | 4/2015 |

(Continued)

OTHER PUBLICATIONS

Dai et al. (Synthetic Communications, 2006, 36, 1829-1835). (Year: 2006).*

(Continued)

*Primary Examiner* — Clare M Perrin
(74) *Attorney, Agent, or Firm* — Bayramoglu Law Offices LLC

(57) ABSTRACT

A synthesis method of an indole derivative capable of efficiently degrading a perfluorinated compound (PFC) and a use of the indole derivative are provided. The synthesis method includes dissolving an appropriate amount of indole, alkylamine, and formaldehyde in an ethanol solution, conducting a reaction at reflux under suitable conditions for a specified period of time with $ZnCl_2$ or glacial acetic acid as a catalyst to form a reaction product, vacuum-drying the reaction product, and purifying the reaction product through column chromatography to obtain a novel indole derivative with a hydrophobic alkyl branch. The present indole derivative has some hydrophobicity and a positively charged amino group that can effectively capture PFCs in contaminated water to produce a sub-nanoscale self-assembled aggregate. Hydrated electrons generated by light irradiation can directly attack PFCs in the aggregate without long-distance mass transfer, improving the utilization rate of hydrated electrons and reduces the ratio of fed materials.

7 Claims, 4 Drawing Sheets

(51) Int. Cl.
*C02F 1/68* (2023.01)
*C02F 101/36* (2006.01)
*C07D 209/14* (2006.01)

(52) U.S. Cl.
CPC ........ *C02F 2305/00* (2013.01); *C07D 209/14* (2013.01)

(56) References Cited

FOREIGN PATENT DOCUMENTS

| CN | 105536198 A | * | 5/2016 | ............. C02F 1/286 |
| CN | 105536198 A | | 5/2016 | |
| CN | 109745962 A | | 5/2019 | |
| CN | 111518011 A | | 8/2020 | |

OTHER PUBLICATIONS

Lajarin-Cuesta et al. (J. Med. Chem., 2016, 59, 6265-6280). (Year: 2016).*
Siavosh Mahboobi, et al., Antimykobakteriell wirksame Indolderivate, Arch Pharm, (Weinheim), 1994, pp. 105,107,113, vol. 327, Issue 2.

* cited by examiner

SYNTHESIS METHOD OF INDOLE DERIVATIVE CAPABLE OF EFFICIENTLY DEGRADING PERFLUORINATED COMPOUND (PFC)

CROSS REFERENCE TO THE RELATED APPLICATIONS

This application is the national phase entry of International Application No. PCT/CN2021/085306, filed on Apr. 2, 2021, which is based upon and claims priority to Chinese Patent Application No. 202010353919.4, filed on Apr. 29, 2020, the entire contents of which are incorporated herein by reference.

TECHNICAL FIELD

The present disclosure relates to the field of efficient degradation of perfluorinated compounds (PFCs), in particular, to a synthesis method of an indole derivative capable of efficiently degrading a PFC and the use of the indole derivative.

BACKGROUND

PFCs are a group of synthetic aliphatic chemicals in which all C (carbon) atoms are saturated with F (fluorine) atoms and are widely used in industrial and commercial products including waxes, varnishes, high-temperature lubricants, protective coatings, foam extinguishing agents, carpets, clothing, furniture, fabrics, and food packaging. Due to the large-scale production and use of PFCs, PFCs are widely detected in the environment, such as in surface water, sediments, atmospheric particulates, and sludge. PFCs can adversely affect infant development and female fertility because PFCs can cause developmental toxicity, endocrine disruption, immunotoxicity, and potential carcinogens for humans due to their environmental persistence and bioaccumulation. Typical PFCs include perfluorooctanoic acid (PFOA) and perfluorooctane sulfonate (PFOS). PFOA and PFOS have been listed on the Stockholm Convention's prohibited and restricted production use list. Therefore, reducing, to the utmost extent, the amount of PFCs in contaminated water to ensure safe drinking water is crucial for ecological and human health.

A C—F bond energy in PFCs can reach 485 kJ/mol, such that most chemical and biological reactions fail to effectively cleavage the C—F bonds of organic fluorides. Although methods based on activated carbon, ion exchange resin, and reverse osmosis (RO) membrane have been used or evaluated to adsorb and exclude PFCs in water/wastewater with considerable efficiencies, the resultant adsorbent or flocculated sludge still needs to be treated by other processes, such as high-temperature incineration and additional chemical degradation. In terms of basic research, more new approaches for degrading PFCs have been proposed, such as advanced oxidation process (AOP), electrochemical oxidation, photocatalytic degradation process, ultrasonic degradation, thermal pyrolysis process, and hydrated electron based reduction defluorination process. Among them, the hydrated electron based reduction approaches exhibit high efficiencies to degrade PFCs, since it performs rapid and thorough degradation efficiency, relatively low energy consumption, easy-operational with simple reaction device requirement. Thus, this technology is promising for actual application. Chinese Patent Application No. 200910051114.8 discloses a method for degrading PFCs through photoreductive defluorination, where reducing substances such as potassium thiosulfate and potassium sulfite are excited through ultraviolet (UV) irradiation to generate hydrated electrons to efficiently reduce PFOA. However, this method needs to be conducted in alkaline and anaerobic conditions, which increases the treatment cost and is difficult to operate in practical applications. Chinese Patent Application No. 201510981853.2 discloses another method for efficiently degrading PFCs, where indoleacetic acid (IAA) is excited by UV irradiation to generate hydrated electrons and organo-modified montmorillonite is added. This method not only improves the degradation and defluorination efficiency of PFOA but also is independent of pH and dissolved oxygen in a solution. IAA is a natural auxin, and thus this treatment method is environmentally friendly. However, the UV/IAA system is still deficient in low hydrated electron utilization efficiency and high chemical dosage requirement. For example, in order to degrade 10 mg/L PFOA, 2.2 g/L organo-montmorillonite and 1 mmol IAA need to be introduced, which would increase the use cost and produce a large amount of sludge. Therefore, it is necessary to develop new hydrated electron reduction technologies based on new indole compounds for degrading PFCs, which is expected to improve the hydrated electron utilization efficiency, reduce the chemical usage, so as to achieve a higher degradation efficiency.

The photo-induced hydrated electron reduction defluorination process is the most efficient method to degrade PFCs in water and is also a development direction for treating PFC-containing water in the future. The existing methods for degrading PFCs through photo-induced hydrated electron production from IAA still have the shortcomings of insufficient hydrated electron utilization and high chemical dosage.

SUMMARY

For this to be achieved, the present disclosure develops a new class of indole derivatives decorate with the alkyl chain, which were synthesized from the indole compound and the long-chain alkyl amines via the Mannich reaction. The final product obtained by the present disclosure is a novel indole derivative with a hydrophobic alkyl branch, and its amino center is positively charged. Such that it can effectively capture PFCs in contaminated water via forming a sub-nanoscale self-assembled aggregate. The hydrated electrons generated by light irradiation can directly attack PFCs in the aggregate without long-distance mass transfer. Therefore, the utilization efficiency of hydrated electrons is greatly improved, and the fed ratio could be largely reduced.

To achieve the above objective, the present disclosure provides the following technical solutions.

A synthesis method of an indole derivative is provided including the following steps: dissolving an appropriate amount of indole, alkylamine, and formaldehyde in an ethanol solution; using $ZnCl_2$ or glacial acetic acid as the catalyst to establish the reflux reaction under suitable conditions for a specified period of time; vacuum-drying the reaction product; and purifying the reaction product through column chromatography to finally obtain the indole derivative.

Further, the alkylamine may include n-hexadecylamine, n-dodecylamine, n-octylamine, or n-amylamine.

The indole, the alkylamine, and the formaldehyde may be in a molar ratio of 1:0.5:1.

The molar ratio of the indole to the $ZnCl_2$ may be 1:0.2.

The molar ratio of the indole to the glacial acetic acid may be 1:2.

Further, the reflux reaction may be conducted at 50° C. to 60° C. for 10 h.

The present disclosure also provides a use of an indole derivative synthesized by the synthesis method described above in the efficient degradation of a PFC.

The present disclosure also provides a method for degrading a PFC with an indole derivative synthesized by the synthesis method described above including the following steps: under aerobic conditions, adding the indole derivative with isopropyl alcohol (IPA) as a cosolvent directly to a PFOA-containing aqueous solution to form a resulting mixture; thoroughly stirring the resulting mixture for 2 h to obtain a reaction solution with suspended nanocomposites; irradiating the reaction solution with a 36 W low-pressure mercury lamp for excitation to allow a reaction for 24 h under stirring.

The molar concentration of the indole derivative may be 5 to 10 times the concentration of the PFOA. The reaction solution may have a pH of 4-7, and the reaction may be conducted at 25° C.

During the reaction, the PFOA concentration and F$^-$ ion concentration may be determined by high-performance liquid chromatography (HPLC) and ion chromatography (IC).

The degradation principle of the present disclosure is as follows:

The indole derivative synthesized by the present disclosure has hydrophobicity and can form a self-assembled nanocomposite in water. In the presence of PFOA, the indole derivative nanocomposite can adsorb or embed PFOA molecules, such that the indole derivative and PFOA are tightly combined. Under the excitation of deep UV irradiation, the indole structure of the indole derivative can be excited to emit electrons to form hydrated electrons in water, accompany with the production of the indole cations. The hydrated electrons can directly attack the adsorbed PFOA in the nanocomposite, instead of reacting with the PFOA in bulk phase after a long-distance migration, which avoids the quenching of hydrated electrons by water molecules, oxygen, and other oxidative species in the solution, and ensures the efficient utilization of hydrated electrons. Since the utilization rate of hydrated electrons is improved, the dosage of the indole derivative can be reduced.

Compared with the prior art, the present disclosure has the following advantages.
1. The present disclosure can lead to high degradation efficiency, low indole derivative consumption, and a high hydrated electron utilization rate. The Chinese application No. 200910051114.8 also disclosed a method based on hydrated electron for degrading PFCs. To achieve a defluorination rate of 60% within 4 h, an alkaline pH condition (pH=9-11) is necessary, and the addition amount of potassium thiosulfate is 20 times the amount of PFOA. The Chinese application No. 201510981853.2 disclosed the method for degrading PFCs using IAA and organo-modified clay as hydrated electron generator. The requirement of IAA is 50 times the amount of PFOA, additionally, 2.2 g/L organo-modified montmorillonite is added. Compared with these two patents, the present disclosure uses the newly synthesized indole derivative for degrading PFOA. The chemical dosage of only 5 to 10 times the amount of PFOA can achieve the complete degradation of the PFOA within 2 h, with the defluorination ratio over 60% within 4 h (as shown in FIG. 4).
2. The degradation application of the present disclosure is suitable for neutral pH conditions and is not disturbed by dissolved oxygen. The solution after degradation is expected to have relatively low toxicity. The underlying mechanism of the present disclosure is that hydrated electrons generated by the indole derivative in the self-assembled nanocomposite can directly attack C—F bonds to achieve high degradation and defluorination efficiencies for PFCs. Therefore, the hydrated electrons produced in the nanocomposite will not be quenched by oxygen and protons in the bulk phase. The degradation/defluorination performance under aerobic and neutral conditions is not significantly different from that under anaerobic and alkaline conditions, which greatly improves the versatility of this method.

DETAILED DESCRIPTION OF THE EMBODIMENTS

The present disclosure is further described below with reference to specific examples.

Example 1

Figure 1:
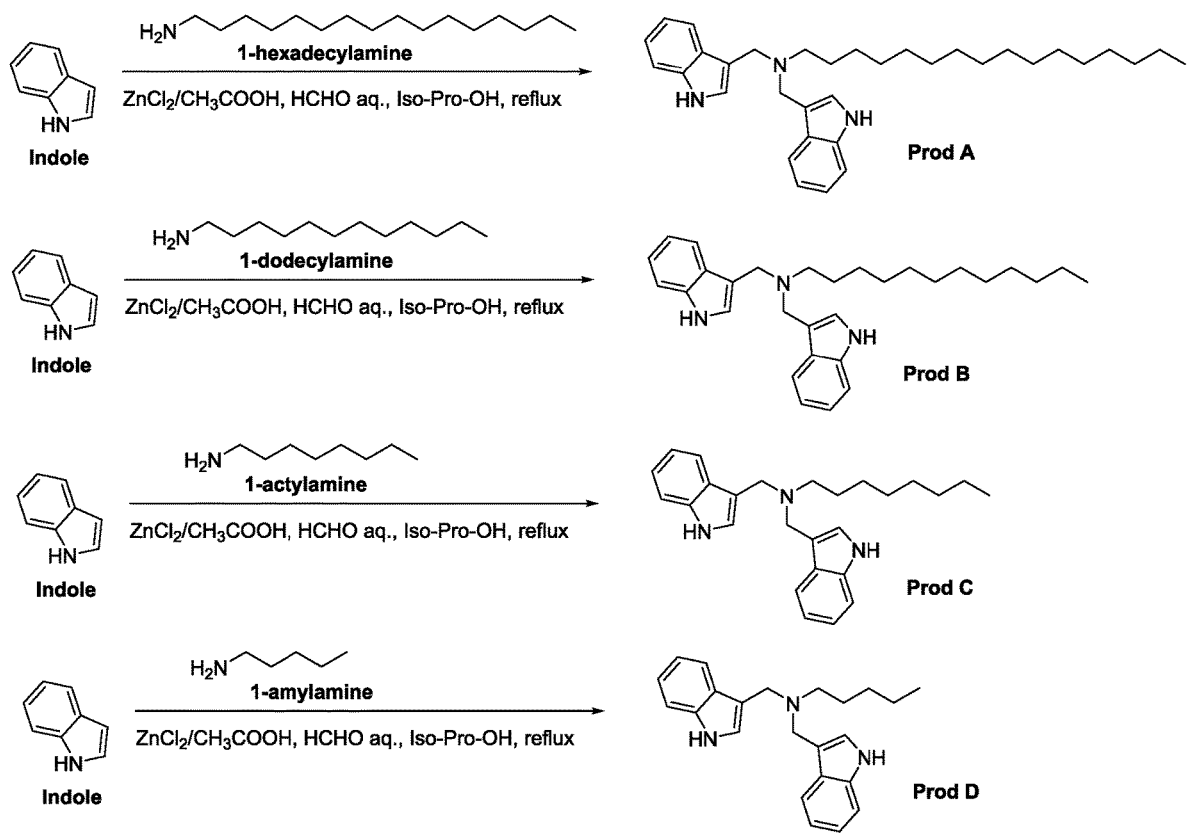
FIG. 1 is a schematic diagram illustrating a synthetic route of the indole derivatives.

Chemical synthesis of a novel indole derivative:

5 g of indole, 5.2 g of n-hexadecylamine, and 3.3 mL of formaldehyde solution with the concentration of 35% were dissolved in 50 mL ethanol. Then, 1.2 g of $ZnCl_2$ was added as the catalyst. The reaction was lasted for 10 h under reflux condition at 55° C. The resulting reaction system was filtered, rotary-evaporated to 10 mL, and subjected to purification through a silica gel column (200 mesh to 300 mesh). Finally, product A (FIG. 1) with a yield of 60% (equals to 3 g).

Example 2

Figure 2:
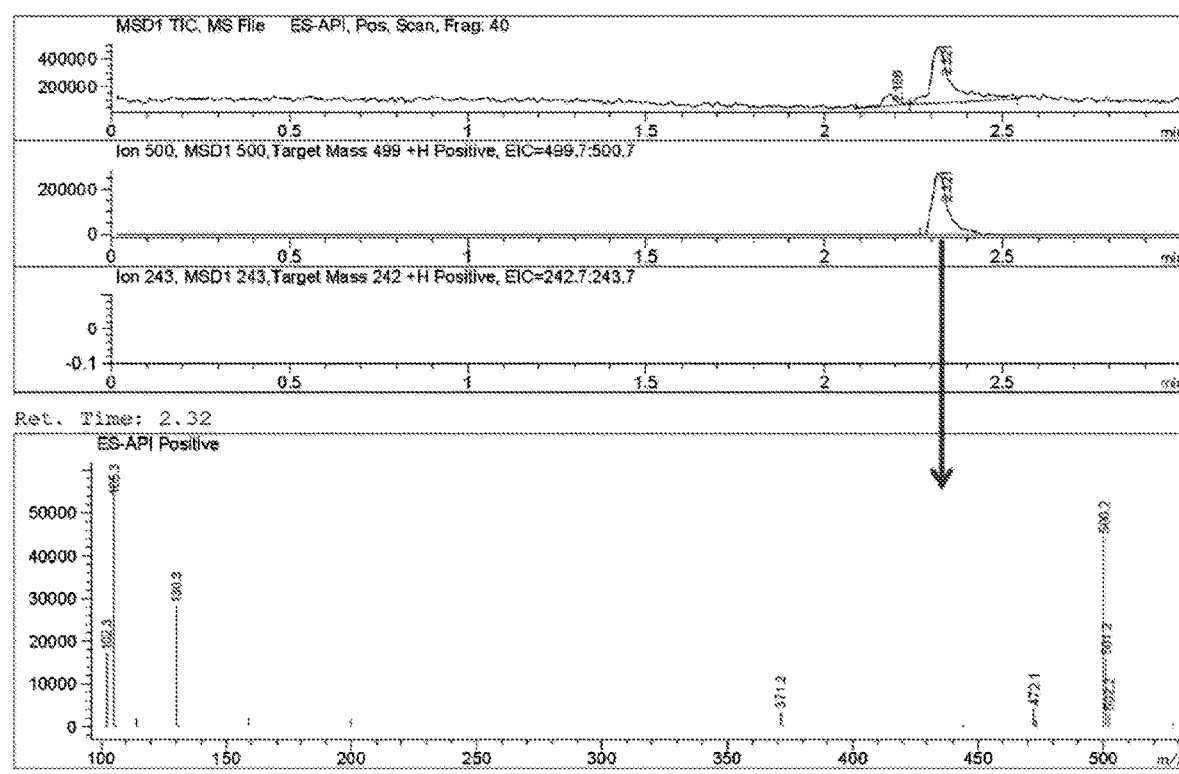
FIG. 2 shows a liquid chromatography-mass spectrometry (LC-MS) spectrum of the synthetic indole derivative.

Chemical synthesis of a novel indole derivative:
(1) The same indole, n-hexadecylamine, and formaldehyde as in Example 1 were adopted as raw materials, 5.1 g of glacial acetic acid was adopted as a catalyst, and the same preparation and purification methods were adopted to finally obtain 9.2 g of product A with the yield of 87%.
(2) Product A was dissolved in IPA at a concentration of 10 mg/L. The purity of product A was determined by liquid chromatography-mass spectrometry (LC-MS). The LC-MS system includes an Agilent 1200 HPLC system, and an Agilent 6120 mass spectrometer equipped with an electrospray ionization (ESI) source. The Waters X-Bridge Shield C18 column (50 mm*4.6 mm*3.5 um) was used for separation. Water (including 0.5% trifluoroacetic acid (TFA)) and acetonitrile (including 0.5% TFA) were adopted as mobile phases for gradient elution at a flow rate of 2 mL/min. The ratio of organic phase increased from 5% to 100% within 1.6 min and held for 1.4 min. The final product A had a purity of >88%. The chromatography-total ion current-mass spectrometry results are shown in FIG. 2.

Figure 3:
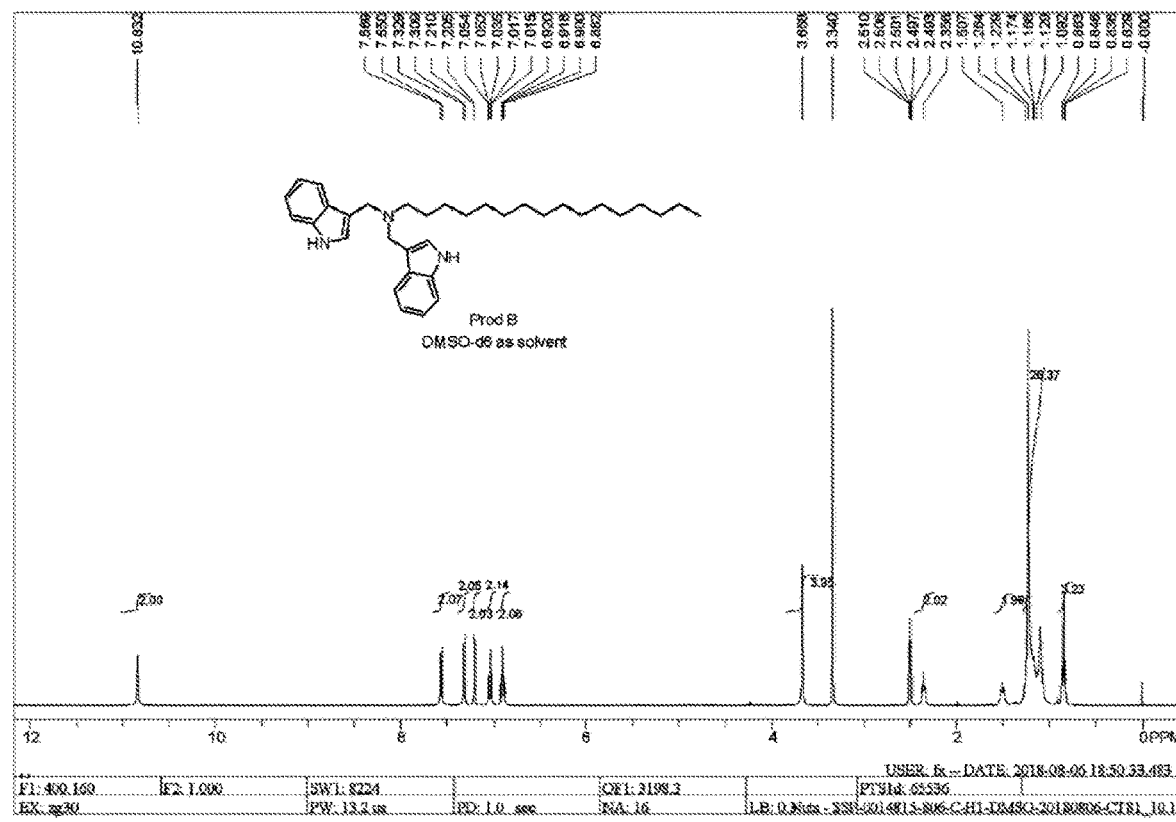
FIG. 3 shows a nuclear magnetic resonance (NMR) spectrum of the synthetic indole derivative.
Figure 4:
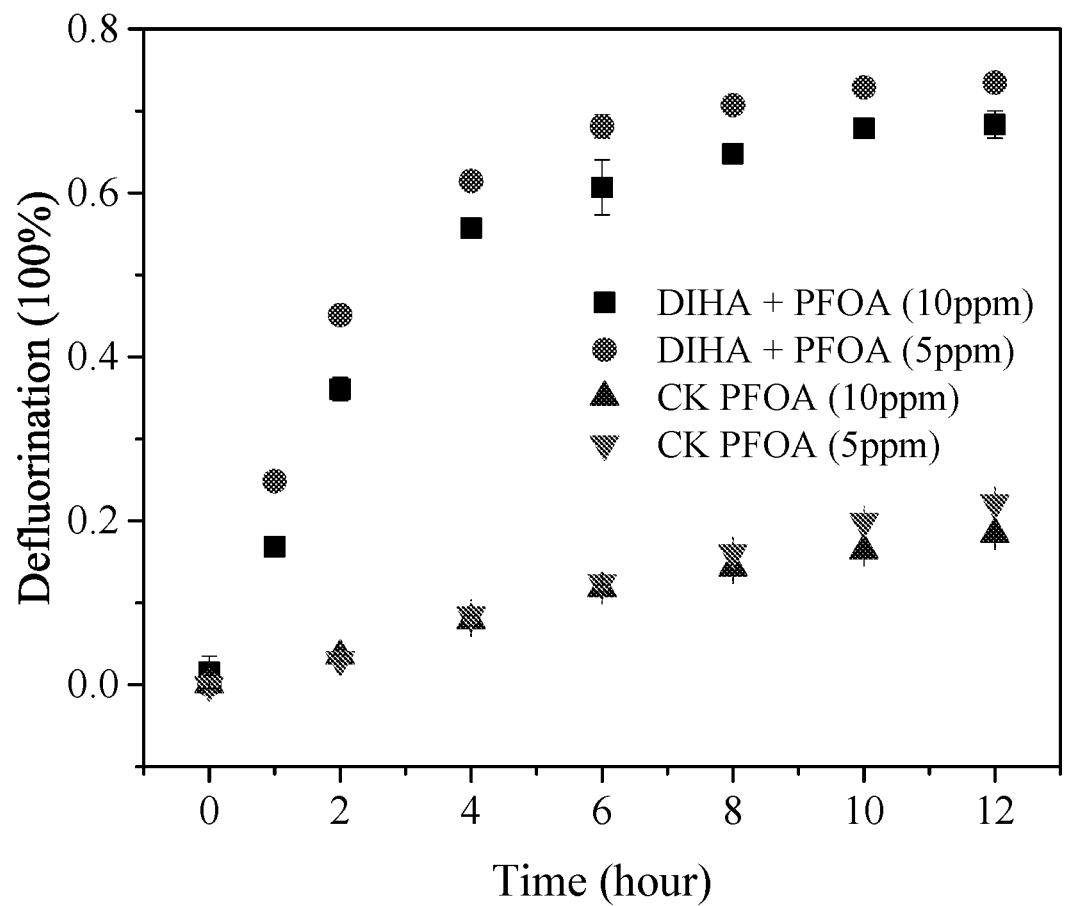
FIG. 4 shows a defluodnation rate of the synthesized indole derivative in PFOA degradation.

(3) Product A was dissolved in dimethyl sulfoxide (DMSO), and a chemical shift of 1H was measured on a Bruker 400 (400 MHz) NMR spectrometer. An NMR spectrum is shown in FIG. 3.

Example 3

The synthesis method is also suitable for the synthesis of derivatives with different alkyl chain lengths. The n-hexadecylamine in Example 2 was replaced by an alkylamine of another carbon chain length, including n-dodecylamine ($H_2N-C_{12}H_{25}$), n-octylamine ($H_2N-C_8H_{17}$), and n-amylamine ($H_2N-O_5H_{11}$). Glacial acetic acid was adopted as the catalyst. The same preparation and purification methods were adopted to synthesize products B, C, and D respectively (FIG. 1), whose yields were each higher than 80%.

Example 4

A method for efficiently degrading PFOA with the synthetic novel indole derivative:

(1) The photodegradation performance of product A on PFCs was tested. The synthetic indole derivative (product A) was firstly dissolved into IPA. The resulting mixture was subjected to an ultrasonic treatment for 10 min to completely dissolve the product A to obtain the IPA based stock solution of the product A with fixed concentration. Under aerobic conditions, a certain amount of the IPA based stock solution of the product A was added to a PFOA containing water with a specified concentration. In the final reaction solution (300 mL), the concentration of PFOA was 10 mg/L (24.2 μmol/L) or 5 mg/L (12.1 μmol/L), the concentration of product A was 121 μmol/L, and the concentration of the IPA as a cosolvent was <0.2% (v/v). The pH of the reaction system was adjusted to 7.0 with 0.1 mol/L NaOH and HCl. The prepared solution was magnetically stirred for 2 h to stabilize the self-assembly system. The reaction solution was transferred into a cylindrical shaped photo-reactor (with a diameter of 5 cm and a height of 25 cm) and magnetically stirred. The reaction temperature was controlled at 25° C. by a constant-temperature water bath in the inner and outer interlayers of the vessel. A 36 W low-pressure mercury lamp was inserted into the cylindrical reaction vessel as the light source to initiate the reaction. The reaction control group was set, that is, only 0.2% IPA (without the synthetic indole derivative) was added to a PFOA reaction solution at 10 mg/L or 5 mg/L. As the reaction proceeding, aliquots were sampled every 1 h to 2 h to determine the residual PFOA concentration and the yield of P ion in the reaction solution.

(2) 5 mL aliquot was collected at each sampling point to determine the residual PFOA concentration and the yield of $F^-$ ion. 2 mL of the sample was transferred to an 8 mL glass bottle, 4 mL of acetonitrile was added, and the resulting mixture was shaken for 30 min to allow extraction, passed through a 0.22 μm PES membrane, and tested by HPLC (Waters 2695). A Waters X-Bridge Shield C18 column (50 mm*4.6 mm*3.5 μm) was used as a separation column, 40% acetonitrile and a 60% ammonium acetate aqueous solution (0.02 mol/L) were adopted as mobile phases, a flow rate was 1 mL/min, a column temperature was 35° C., and a conductivity detector was adopted. The remaining 3 mL of the sample was taken to determine an $F^-$ ion concentration. The sample was diluted 3 times with ultrapure water (UPW) to 9 mL, then passed through a 0.22 μm nylon filter membrane, a P column, an RP column, and a Na column successively, and subjected to IC (ICS-900, DIONEX). An anion-exchange column (DionexIonPac AS23, 4 mm×250 mm) was used as a separation column. $NaHCO_3$ (1.6 mmol/L) and $Na_2CO_3$ (10 mmol/L) aqueous solutions were adopted as the mobile phase at a flow rate of 1 mL/min. The suppressor current was set as 51 mA. The PFOA and $F^-$ ion concentrations were quantified by an external standard method.

The above descriptions are merely preferred examples of the present disclosure, but do not impose restrictions to the present disclosure in any form. Any person skilled in the art can make any simple modifications, equivalent replacements, and improvements to the above examples according to the technical essence of the present disclosure without departing from the scope of the technical solutions of the present disclosure. Such simple modifications, equivalent replacements, and improvements still fall within the protection scope of the technical solutions of the present disclosure.

What is claimed is:

1. A method for degrading a perfluorinated compound (PFC) with an indole derivative comprising the following steps:
    dissolving indole, alkylamine, and formaldehyde in an ethanol solution, and conducting a reaction under reflux with $ZnCl_2$ or glacial acetic acid as a catalyst to form a reaction product;
    vacuum-drying the reaction product, and purifying the reaction product through a column chromatography to obtain the indole derivative; and
    under aerobic conditions, adding the indole derivative with isopropyl alcohol (IPA) as a cosolvent directly to a perfluorooctanoic acid (PFOA)-containing aqueous solution to obtain a resulting mixture, thoroughly stirring the resulting mixture for 2 h to obtain a reaction solution with suspended particles, and irradiating the reaction solution with a 36 W low-pressure mercury lamp for an excitation to allow a reaction for 24 h under stirring.

2. The method for degrading the PFC with the indole derivative according to claim 1, wherein a molar concentration of the indole derivative is 5 to 10 times a concentration of the PFOA; the reaction solution has a pH of 4 to 7; and the reaction is conducted at 25° C.

3. The method according to claim 1, wherein in a synthesis of the indole derivative, the alkylamine comprises n-hexadecylamine, n-dodecylamine, n-octylamine, or n-amylamine.

4. The method according to claim 1, wherein in a synthesis of the indole derivative, the indole, the alkylamine, and the formaldehyde are in a molar ratio of 1:0.5:1.

5. The method according to claim 1, wherein in a synthesis of the indole derivative, a molar ratio of the indole to the $ZnCl_2$ is 1:0.2.

6. The method according to claim 1, wherein in a synthesis of the indole derivative, a molar ratio of the indole to the glacial acetic acid is 1:2.

7. The method according to claim 1, wherein in a synthesis of the indole derivative, the reaction under reflux is conducted at 50° C. to 60° C. for 10 h.

* * * * *